United States Patent [19]

Horner et al.

[11] 4,320,228

[45] Mar. 16, 1982

[54] PREPARATION OF OLEFINICALLY UNSATURATED CARBONYL COMPOUNDS AND ALCOHOL

[75] Inventors: Michael Horner, Neustadt; Matthias Irgang, Mannheim; Axel Nissen, Leimen, all of Fed. Rep. of Germany

[73] Assignee: BASF Aktiengesellschaft, Fed. Rep. of Germany

[21] Appl. No.: 166,858

[22] Filed: Jul. 8, 1980

[30] Foreign Application Priority Data

Aug. 24, 1979 [DE] Fed. Rep. of Germany ....... 2934250

[51] Int. Cl.$^3$ ...................... C07C 47/21; C07C 29/17
[52] U.S. Cl. ..................................... 568/459; 568/881
[58] Field of Search ................................. 568/459, 881

[56] References Cited

U.S. PATENT DOCUMENTS

| | | | |
|---|---|---|---|
| 3,463,818 | 8/1969 | Blumenthal | 568/459 |
| 3,860,657 | 1/1975 | Easter et al. | 568/459 |
| 4,237,072 | 12/1980 | Aviron-Violet | 568/459 |

FOREIGN PATENT DOCUMENTS

| | | | |
|---|---|---|---|
| 2706862 | 8/1977 | Fed. Rep. of Germany | 568/459 |
| 2314911 | 2/1977 | France | 568/459 |
| 420608 | 8/1974 | U.S.S.R. | 568/459 |

*Primary Examiner*—Werren B. Lone
*Attorney, Agent, or Firm*—Keil & Witherspoon

[57] ABSTRACT

Olefinically unsaturated carbonyl compounds $R^1$—CH$R^2$—CH$R^3$—C($R^4$)O (I) and alcohols $R^1$—CH$R^2$—CH$R^3$—CH($R^4$)—OH (II) (where $R^1$ is an olefinically unsaturated organic radical, and $R^2$, $R^3$ and $R^4$ are H or $C_1$-$C_4$-alkyl) are prepared by hydrogenating the carbonyl compounds $R^1$—C$R^2$=C$R^3$—C($R^4$)O (III) in the liquid phase with hydrogen, using a catalyst system comprising, firstly, Pd and, secondly, Ru, Rh, Os, Ir or Pt, in the presence of from 5 to 40% by weight, based on (III), of a tertiary amine, under a hydrogen pressure of from 1 to 20 bar is predominantly (I) is to be obtained and from 20 to 150 bar if predominantly (II) is to be obtained.

The process is of particular importance for the hydrogenation of citral (IIIa) to give citronellal (Ia) or citronellol (IIa), the preferred amine being trimethylamine.

7 Claims, No Drawings

PREPARATION OF OLEFINICALLY UNSATURATED CARBONYL COMPOUNDS AND ALCOHOL

The present invention relates to an improved process for the preparation of olefinically unsaturated carbonyl compounds and alcohols of the general formulae I and II respectively,

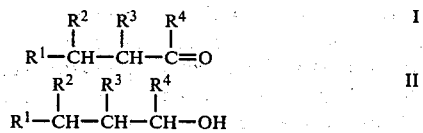

where $R^1$ is an olefinically unsaturated organic radical and $R^2$, $R^3$ and $R^4$ are hydrogen or $C_1$–$C_4$-alkyl, by hydrogenating an $\alpha,\beta$-unsaturated carbonyl compound of the general formula III

in the liquid phase by means of hydrogen in the presence of nobel metal catalysts. Specifically, the invention relates to the hydrogenation of citral (IIIa)

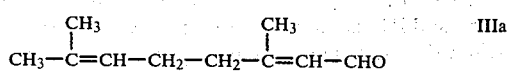

to give citronellal (Ia)

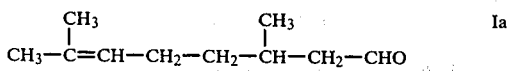

or to give citronellol (IIa)

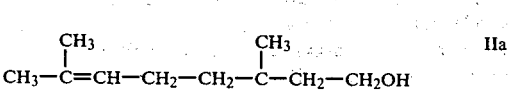

It is generally known, and therefore does not require more detailed discussion here, that the carbonyl group of $\alpha,\beta$-unsaturated carbonyl compounds can be hydrogenated selectively, or substantially selectively, ie. without attacking the olefinic double bond, to the corresponding alcohol group by using a ruthenium, rhodium, osmium, iridium or platinum catalyst and that under these conditions other olefinic double bonds, in addition to the particularly sensitive $\alpha,\beta$-double bond, remain more or less intact. A particularly economical process of this type, wherein a tertiary amine is present during the hydrogenation, forms the subject matter of German Patent Application No. P 29 34 251.6, which enjoys the same priority date as the present application, and which corresponds to U.S. application Ser. No. 67,706.

If palladium is used instead of the said hydrogenation catalysts, it is—as is also generally known—mainly the olefinic double bonds which undergo hydrogenation, whilst the carbonyl group is attacked only to a lesser degree, if at all. Particularly good results are achieved by the process of the earlier U.S. patent application Ser. No. 67,706, wherein the hydrogenation is carried out in the presence of from 15 to 50% by weight, based on the amount of carbonyl compound employed, of a tertiary amine.

If a carbonyl compound III was to be converted to a carbonyl compound I and an alcohol II by the prior art processes, two separate hydrogenations, the one selective in respect of the carbonyl group and the other selective in respect of the $\alpha,\beta$-unsaturated olefinic double bond, would have to be carried out in succession. Since this is obviously a technological disadvantage, a plurality of processes for simultaneous hydrogenation has already been proposed.

If, using the method disclosed in Research of India, 17/1 (1972), page 11, a Cu/Cr catalyst is employed for this purpose, the hydrogenation of citral gives citronellol yields of only 70%. With Raney nickel (U.S. Pat. No. 3,680,657 and German Laid-Open Application DOS No. 2,706,862) the hydrogenation of citral to citronellol takes place too slowly and insufficiently selectively. The good yields of up to 94% attainable by the process of German Laid-Open Application DOS No. 2,706,862 when hydrogenating citral to citronellol with chromium-activated Raney nickel can only be achieved with uneconomically long reaction times and by using large amounts of catalyst, so that this process is also industrially unattractive.

It is an object of the present invention to provide an improved process for the simultaneous hydrogenation of the double bonds in the

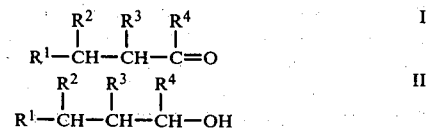

of a carbonyl compound III.

It is a further object of the invention to provide a process for hydrogenating a carbonyl compound III not only to give the alcohol II, but also, according to choice, to give the intermediate, namely the $\alpha,\beta$-unsaturated carbonyl compound I, in particular by using the same catalyst system and with only slight modification of the reaction conditions. It is a specific object of the invention to improve, and simplify the technology, of the industrially particularly important hydrogenation of citral IIIa, to give the versatile fragrances citronellal Ia and citronellol IIa.

We have found that these objects are achieved and that olefinically unsaturated carbonyl compounds and alcohols of the general formulae I and II

where $R^1$ is an olefinically unsaturated organic radical and $R^2$, $R^3$ and $R^4$ are hydrogen or $C_1$–$C_4$-alkyl, are obtained in a technologically advantageous manner, and with economic advantages, by hydrogenating an $\alpha,\beta$-unsaturated carbonyl compund III $$R^1-\overset{R^2}{\underset{|}{C}}=\overset{R^3}{\underset{|}{C}}-\overset{R^4}{\underset{|}{C}}=O \qquad III$$

in the liquid phase with hydrogen in the presence of noble metal catalysts if the hydrogenation is carried out in the presence of a catalyst system comprising, firstly, palladium, and, secondly, ruthenium, rhodium, osmium, iridium or platinum, as the active constituents, and of from 5 to 40% by weight, based on the amount of III, of a tertiary amine, using a hydrogen pressure of from 1 to about 20 bar if predominantly compound I is to be obtained and of from about 20 to 150 bar if predominantly compound II is to be obtained.

It is an essential feature of the process that because of the presence of the tertiary amine the olefinic double bond in the radical $R^1$ remains virtually unattacked.

In principle, based on our observations to date, any tertiary amine may be used, so that the chemical nature of the amine is immaterial provided it is free from functional groups which can undergo other reactions with the reactants. Examples of suitable amines are aliphatic tertiary amines of a total of 3 to 30 carbon atoms, especially trimethylamine and also triethylamine, triethanolamine and trihexylamine, cyclic tertiary amines, eg. N-methylpiperidine, N-methylmorpholine and N,N'-dimethylpiperazine, aliphatic-cycloaliphatic tertiary amines, eg. N,N-dimethylcyclohexylamine, aliphatic-araliphatic tertiary amines, eg. N,N-dimethylbenzylamine, aliphatic-aromatic tertiary amines, eg. N,N-dimethylaniline and heterocyclic-aromatic tertiary amines, eg. pyridine and quinoline.

For economic reasons, the cheapest possible amines whose boiling point is either substantially below or substantially above those of the products to be obtained should be used, since in these caes either the amines or the products can easily be distilled from the reaction mixture.

The amount of amine employed is preferably from 10 to 30% by weight, based on starting material III.

The catalyst combination required for the hydrogenation consists, firstly, of the component Pd and, secondly, of the component Ru, Rh, Os, Ir or Pt. These components may be employed separately, as unsupported or supported catalysts, or conjointly as combined supported catalysts. The use of separate supported catalysts is preferred, since such catalysts are commercially available.

According to our observations to date, all commercial catalysts of the above type are of similar suitability, so that if the type of catalyst is changed the operating conditions require only slight change, if any.

Pd is preferably employed in an amount of from 0.001 to 0.1, especially from 0.005 to 0.1, % by weight, and the other platinum metals in an amount of from 0.002 to 0.2, especially from 0.01 to 0.2, % by weight, in each case expressed as metal and based on the amount of starting compound III. The weight ratio of Pd to the other noble metals is advantageously from 1:2 to 1:10. If a ratio outside this range is used, the two hydrogenation reaches (hydrogenation of the carbonyl group and of the $\alpha,\beta$-double bond) take place at substantially different speeds, so that if the hydrogenation is stopped prematurely an excess of one of the partially hydrogenated products is always obtained; this effect may under certain circumstances be desirable, if several hydrogenation products are to be prepared simultaneously and in a certain ratio, for example geraniol or nerol or citronellal simultaneously with citronellol when hydrogenating citral. Since most commercial catalysts are supported catalysts with active charcoal as the carrier and with a metal content of 5% by weight, such catalysts are preferred, for economic reasons.

The reaction is preferably carried out in the presence of a solvent. The amount of solvent is in general from 10 to 300, preferably from 25 to 150, % by weight of III. Suitable solvents are all inert liquids in which I, II and III, and the tertiary amine, are soluble. Examples include the tertiary amines themselves, and alcohols, eg. methanol and ethanol, ethers, acetone and hydrocarbons which are liquid under the reaction conditions, eg. hexane and cyclohexane. Methanol is preferred, especially if trimethylamine is used as the base, since in that case the working-up of the reaction mixture proves particularly simple.

In general, the hydrogenation is carried out at from 20° to 150° C. If it is desired to prepare the carbonyl compounds I, the hydrogen pressure used is from 1 to about 20, preferably 10, bar, whilst if the alcohols II are required, a suitable pressure is from about 20 to 200 bar. If a pressure of from 10 to 20 bar is employed, or if the reaction is stopped prematurely, both products are obtained together, which may be desirable under certain circumstances. It is to be emphasized that the formation of I or II, under otherwise identical reaction conditions in respect of, eg. temperature, type of catalyst system and ratio of its components, essentially only depends on the hydrogen pressure, ie. it is possible, by means of the simple technological measure of changing the pressure, to convert the same starting material, in the same hydogenation apparatus, either to a compound of type I or to a compound of type II, as required, or even, if desired, to a mixture of these compounds.

Within the scope of the general definition, $R^1$ in compound III may in principle have any meaning. If the olefinic double bonds in such radicals $R^1$ are conjugated with the

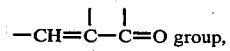

it partially also undergoes hydrogenation, whilst isolated double bonds are not attacked. Examples of $R^1$ are alkenyl of 1 to 20 carbon atoms, cyclopentenyl and cyclohexenyl. These radicals may in turn be substituted, for example by alkyl, alkoxy, carbalkoxy, acyl, hydroxyl, carboxyl, nitrile, amino and halogen. Since the principle of the process is unaffected by the nature of the substituents $R^1$ to $R^4$, it is superfluous to give a separate recital of the possible starting compounds III. The other aspects of their chemical nature are immaterial in the present context, but in practice the compounds used are mostly unbranched or branched monounsaturated or polyunsaturated alkenals and alkenones of 4 to 40 carbon atoms, having the general formula III.

EXAMPLE

Preparation of Citronellol 43 g portions of pure citral (3,7-dimethylocta-2,6-dien-1-al) were hydrogenated in the presence of a mixture of a commercial Pd/active charcoal supported catalyst containing 5% by weight of Pd and a commercial supported catalyst containing 5% by weight of one of the other platinum metals on active charcoal. After removing the catalyst, the reaction products were distilled, leaving the high-boiling residues, and the nature and amount of the products was determined by gas chromatography on the distillate.

The experimental conditions and the results are shown in the Table, where comparative experiments are marked "C".

TABLE

| Experiment No. | Type | Catalyst Weight ratio | Amount g | Amine | Methanol g | Pressure g | Temp. bar | Duration °C. | Conversion[1] h | Citronellol % | Citronellal | Yield, in %, of Geraniol/Nerol | Dimethyloctanol[2] | Residue |
|---|---|---|---|---|---|---|---|---|---|---|---|---|---|---|
| 1 | Pd/Ru | 1:9 | 1.0 | NMe$_3$[3] | 8 | 16 | 50 | 75 | 5 | 100 | 93 | — | 4 | 1 | 1 |
| 2 | Pd/Ru | 1:3 | 1.0 | NMe$_3$ | 8 | 16 | 50 | 75 | 6 | 100 | 94 | 2 | 3 | — | 1 |
| 2C | Pd/Ru | 1:3 | 1.0 | — | — | 16 | 50 | 75 | 8 | 100 | 3 | — | 1 | 95 | 1 |
| 3 | Pd/Ru | 1:9 | 1.0 | NMe$_3$ | 8 | 16 | 30 | 75 | 10 | 100 | 91 | 6 | 2 | — | 1 |
| 4 | Pd/Ru | 1:1 | 1.0 | NEt$_3$[4] | 8 | — | 100 | 100 | 5 | 100 | 90 | 5 | 3 | 1 | 1 |
| 5 | Pd/Ru | 1:3 | 1.0 | DMA[5] | 8 | 16 | 100 | 100 | 4 | 100 | 87 | 4 | 8 | — | 1 |
| 6 | Pd/Pt | 1:3 | 0.1 | NMe$_3$ | 8 | 16 | 50 | 100 | 12 | 100 | 91 | 4 | 3 | 1 | 1 |
| 7 | Pd/Pt | 1:3 | 0.2 | NMe$_3$ | 8 | 16 | 50 | 100 | 10 | 100 | 91 | 1 | 5 | 1 | 1 |
| 8 | Pd/Ir | 1:3 | 1.0 | NMe$_3$ | 8 | 16 | 100 | 100 | 4 | 100 | 90 | — | — | 9 | 1 |
| 9 | Pd/Os | 1:9 | 1.0 | NMe$_3$ | 8 | 16 | 100 | 100 | 5 | 100 | 89 | 7 | 3 | — | 1 |
| 10 | Pd/Pt | 1:3 | 0.2 | NMe$_3$ | 8 | 16 | 6 | 75 | 7 | 100 | 2 | 90 | 6 | — | 1 |
| 11 | Pd/Pt[6] | 1:3 | 0.2 | NMe$_3$ | 8 | 16 | 50 | 100 | 6 | 100 | 92 | 2 | 4 | 1 | 1 |

[1] based on citral
[2] <1% of dimethyloctanal
[3] Me = methyl
[4] Et = ethyl
[5] N,N-Dimethylaniline
[6] Mixed catalyst produced by precipitating Pt from PtCl$_4$ solution onto a Pd/active charcoal catalyst

We claim:

1. A process for the preparation of olefinically unsaturated carbonyl compounds of the formula I

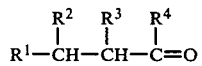

where R$^1$ is an olefinically unsaturated organic radical and R$^2$, R$^3$ and R$^4$ are hydrogen or C$_1$-C$_4$-alkyl, which comprises: hydrogenating an α,β-unsaturated carbonyl compound III

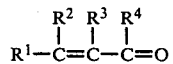

in the liquid phase by means of hydrogen in the presence of a catalyst system comprising, firstly, palladium, and, secondly, ruthenium, rhodium, osmium, iridium or platinum, as the active constituents, and of from 5 to 40% by weight, based on the amount of III, of a tertiary amine, wherein a hydrogen pressure of from 1 to about 20 bar is used.

2. The process of claim 1, wherein citral (3,7-dimethylocta-2,6-dien-1-al, IIIa) is hydrogenated to citronellal (3,7-dimethyloct-6-en-1-al, Ia).

3. The process of claim 2, wherein citral is hydrogenated to citronellal at a hydrogen pressure of from about 1 to 10 bar.

4. A process for the preparation of olefinically unsaturated alcohols of the formula

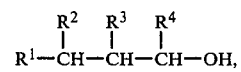

where R$^1$ is an olefinically unsaturated organic radical and R$^2$, R$^3$ and R$^4$ are hydrogen or C$_1$-C$_4$-alkyl which comprises hydrogenating an α,β-unsaturated carbonyl compound III

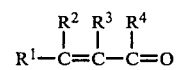

in the liquid phase by means of hydrogen in the presence of a catalyst system comprising, firstly, palladium, and, secondly, ruthenium, rhodium, osmium, iridium or platinum, as the active constituents, and of from 5 to 40% by weight, based on the amount of III, of a tertiary amine, wherein a hydrogen pressure of from about 20 to 150 bar is used.

5. The process of claim 1 or 4, wherein trimethylamine is used as the tertiary amine.

6. The process of claim 4, wherein citral is hydrogenated to citronellol (3,7-dimethyloct-6-en-1-ol, IIa) at a hydrogen pressure of about 20 to 150 bar.

7. The process of claim 3 or 6, wherein trimethylamine is used as the tertiary amine.

* * * * *